United States Patent [19]

Ott et al.

[11] 4,087,530
[45] May 2, 1978

[54] SUBSTITUTED 6-PHENYL-OCTAHYDROBENZO [C] [1,6] NAPHTHYRIDINES

[75] Inventors: Hans Ott, Pfeffingen; Süess, Rudolf, Bettingen, both of Switzerland

[73] Assignee: Sandoz Ltd., Basel, Switzerland

[21] Appl. No.: 670,111

[22] Filed: Mar. 25, 1976

Related U.S. Application Data

[63] Continuation-in-part of Ser. No. 545,540, Jan. 30, 1975, abandoned.

[30] Foreign Application Priority Data

Feb. 5, 1974 Switzerland ............... 1550/74
Sep. 17, 1975 United Kingdom ........ 38177/75
Sep. 17, 1975 United Kingdom ........ 18178/75

[51] Int. Cl.² ............... C07D 217/04; A61K 31/47
[52] U.S. Cl. ............... 424/258; 260/287 CF; 260/288 CF
[58] Field of Search ............ 260/287 CF, 288 CF; 424/258

[56] References Cited

U.S. PATENT DOCUMENTS 3,862,153  1/1975  Ott et al. ............... 260/243 C
3,899,494  8/1975  Ott et al. ............... 260/243 C

FOREIGN PATENT DOCUMENTS

56698/71  2/1927  Japan.

Primary Examiner—Nicholas S. Rizzo

Attorney, Agent, or Firm—Gerald D. Sharkin; Robert S. Honor; Thomas O. McGovern

[57] ABSTRACT

This invention provides new compounds of formula I,

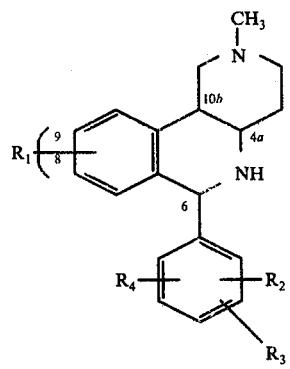

wherein the indicated radical in the 8 or 9 position of the benzonaphthyridine structure ($R_1$) is hydrogen, alkoxy of 1 to 4 carbon atoms or hydroxy, and $R_2$, $R_3$ and $R_4$ are selected in certain combinations from hydrogen, alkyl of 1 to 4 carbon atoms, alkoxy of 1 to 4 carbon atoms, benzyloxy, hydroxy, halogen, nitro, amino, dimethylamino, or —NHCOR$_5$ wherein $R_5$ is hydrogen or alkyl of 1 to 4 carbon atoms, useful as bronchospasmolytics.

72 Claims, No Drawings

SUBSTITUTED 6-PHENYL-OCTAHYDROBENZO [c] [1,6] NAPHTHYRIDINES

This is a continuation in part of our copending application Ser. No. 545,540 of Jan. 30, 1975 now abandoned.

The present invention relates to new heterocyclic compounds.

In accordance with the invention there are provided new compounds of formula I,

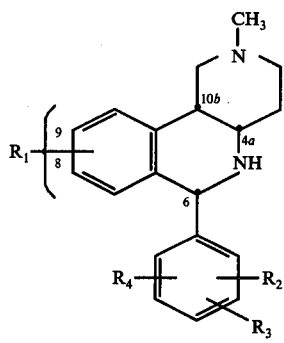

wherein the indicated radical in the 8 or 9 position of the benzonaphthyridine structure ($R_1$) is hydrogen, alkoxy of 1 to 4 carbon atoms or hydroxy, and
(i)
$R_2$ is hydrogen, alkyl of 1 to 4 carbon atoms, alkoxy of 1 to 4 carbon atoms, benzyloxy, hydroxy, halogen, nitro, amino, dimethylamino, or —$NHCOR_5$ wherein $R_5$ is hydrogen or alkyl of 1 to 4 carbon atoms, and
$R_3$ and $R_4$ are hydrogen, or
(ii)
$R_2$ is alkyl of 1 to 4 carbon atoms, alkoxy of 1 to 4 carbon atoms, benzyloxy, hydroxy, halogen or nitro,
$R_3$ is alkyl of 1 to 4 carbon atoms, alkoxy of 1 to 4 carbon atoms, benzyloxy, hydroxy or chlorine, and
$R_4$ is hydrogen,
(iii)
$R_2$, $R_3$ and $R_4$ are, independently, alkoxy of 1 to 4 carbon atoms or benzyloxy, or
(iv)
$R_2$, $R_3$ and $R_4$ are, independently, alkyl of 1 to 4 carbon atoms, or
(v)
$R_2$, $R_3$ and $R_4$ are hydroxy, with the proviso that (i) when one of the radicals $R_2$, $R_3$ and $R_4$ is benzyloxy, the indicated radical in the 8 or 9 position of the benzonaphthyridine structure ($R_1$) is hydrogen or alkoxy of 1 to 4 carbon atoms, (ii) when the indicated radical in the 8 or 9 position of the benzonaphthyridine structure ($R_1$) is other than hydrogen or alkoxy and is in the 9 position, each of the radicals $R_2$, $R_3$ and $R_4$ is other than alkoxy of 1 to 4 carbon atoms, and (iii) when one of the radicals $R_2$ and $R_3$ is benzyloxy or alkoxy of 1 to 4 carbon atoms, the remaining radical $R_2$ or $R_3$ is other than hydroxy.

Any alkyl or alkoxy substituents of the 6-phenyl radical especially contain 1 or 2, preferably 1 carbon atom.

When $R_1$ is alkoxy of 1 to 4 carbon atoms, this especially contains 1 or 2, preferably 1 carbon atom.

When $R_5$ is alkyl of 1 to 4 carbon atoms, this radical especially denotes methyl, ethyl, or an α-branched alkyl radical such as isopropyl or tert.butyl.

When the radical $R_2$ is halogen, this signifies fluorine, chlorine or bromine, preferably fluorine or chlorine.

As may be seen from the formulae, the hydrogen atoms in the 4a, 6 and 10b positions of the benzonaphthyridine structure are in the cis position.

Further, in accordance with the invention a compound of formula I may be obtained by a process comprising
(a) reducing a compound of formula II,

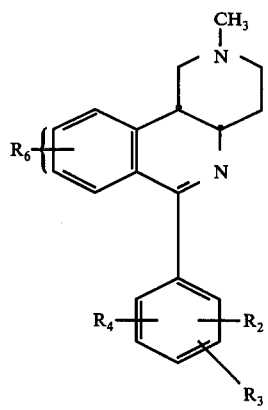

wherein
$R_6$ is in the 8 or 9 position of the benzonaphthyridine structure and is hydrogen, alkoxy of 1 to 4 carbon atoms, hydroxy, or an ether radical capable of being split under the reaction conditions to form a hydroxy radical, and
$R_2$, $R_3$ and $R_4$ are as defined above with the proviso thereto, or b) treating a compound of formula III,

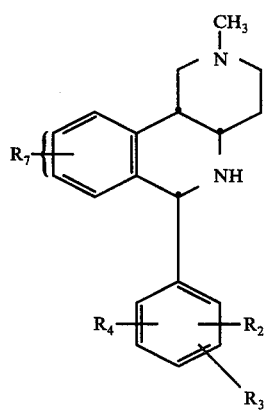

wherein
$R_2$, $R_3$, $R_4$ are as defined above with the proviso thereto,
$R_7$ is an ether radical capable of being split under the reaction conditions to form a hydroxy radical, under the conditions of an ether splitting, to produce a compound of formula Ia,

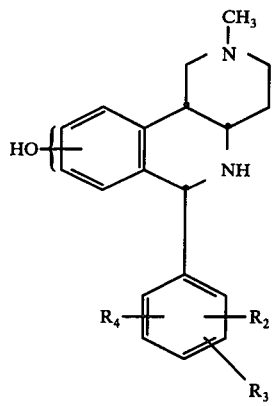

Ia wherein $R_2$, $R_3$ and $R_4$ are as defined above with the proviso thereto and the further proviso that (iv) each of $R_2$, $R_3$ and $R_4$ is other than benzyloxy.

The octahydrobenzo [c][1,6]naphthyridine derivatives produced in accordance with the processes described above, may be isolated in the usual manner and purified in accordance with known methods.

Process variant a) may be effected in conventional manner for the reduction of similar double bonds, with or without ether splitting, in similar compounds.

When $R_6$ is an ether group in the 8 or 9 position of the benzonaphthyridine structure, capable of being split off under the reaction conditions, this group preferably signifies an ether group capable of being split off hydrogenolytically, especially in the presence of a metal catalyst such as platinum or palladium. Examples of such $R_6$ groups are the benzyloxy group, and benzyloxy groups substituted on the phenyl ring or alkylated in α position.

The reaction may be effected with a complex alkali metal hydride in a suitable solvent, e.g. sodium borohydride in methanol or ethanol, or lithium aluminium hydride in ether, tetrahydrofuran, dioxane or dimethoxyethane. The reduction is preferably effected at an elevated temperature, e.g. between about 50° and 100° C. When these reaction conditions are used, it is convenient to chose as starting material compounds of formula II wherein $R_6$ is hydrogen, alkoxy of 1 to 4 carbon atoms or hydroxy. The reduction products are isolated and purified in accordance with known methods, for example after decomposition of the excess reducing agent and the resulting complex by shaking between an aqueous solution and an organic solvent immiscible with this aqueous solution, such as chloroform or ethyl acetate.

The reduction may also be effected by catalytic hydrogenation, e.g. over platinum or palladium or platinum oxide. There may be present an inert solvent, e.g. a lower alkanol such as ethanol or methanol. The reaction is preferably effected at room temperature and e.g. at normal pressure or an elevated pressure. The hexahydrobenzo-[c][1,6]naphthyridine derivatives to be reduced are preferably used in free base form.

Under the latter conditions, any benzyloxy groups and/or ether groups capable of being split off under these conditions, which may be present in the compounds of formula II, are converted into hydroxy groups; in this case the benzyloxy group is conveniently used as ether group capable of being split off, and palladium is conveniently used as catalyst.

When platinum is used as catalyst and a benzyloxy radical is present in the compound of formula II, the 5/6 double bond may be reduced selectively without splitting of the benzyloxy radical.

Further, under the conditions of a catalytic hydrogenation any nitro group is reduced to the amino group or, when formaldehyde is present in the reaction mixture, to the dimethylamino group. The production of compounds of formula I wherein $R_2$ is the nitro group, is therefore conveniently effected with complex hydrides when process variant a) is used.

After the hydrogen take up is complete, the catalyst is filtered off, the filtrate is evaporated to dryness, and the crude octahydro compound obtained as residue is purified in accordance with known methods.

The reduction of the 5/6 double bond takes place stereospecifically in any case; compounds of formula I wherein the hydrogen atoms in positions 4a, 6 and 10b are all in a cis position to one another, are obtained.

Process variant b) is an ether splitting. It may be effected in a manner analogous to known methods for the ether splitting of analogous compounds.

Thus, for example, the ether splitting may be effected with a Lewis acid, e.g. boron tribromide or aluminium chloride. The reaction is preferably effected in an inert organic solvent, e.g. a halogenated hydrocarbon such as methylene chloride or carbon tetrachloride, or an aromatic hydrocarbon such as toluene or benzene. The temperature may be from about −80° to 70° C.

The ether splitting may alternatively be effected with a strong mineral acid, e.g. hydrobromic or hydriodic acid. The reaction is preferably effected at an elevated temperature, e.g. between about 50° and 150° C, for example at the boiling temperature of the reaction mixture. An inert solvent may optionally be used.

An ether group in the 8 position of the benzonaphthyridine structure may be split off selectively, without the splitting of any alkoxy groups on the non-condensed phenyl ring, by carrying out the splitting with a mineral acid under milder conditions, e.g. with a dilute mineral acid at an elevated temperature, e.g. with dilute hydrobromic acid at about 80° to 150° C.

When the groups to be split are ether groups capable of being split off hydrogenolytically, e.g. the benzyloxy group, these are conveniently converted into hydroxy groups by catalytic hydrogenation in the presence of a palladium catalyst. This is preferably effected in an inert organic solvent, e.g. in a lower alkanol such as methanol or ethanol, in ethyl acetate or in glacial acetic acid. The temperature may be from about 20° to 100° C. The reaction is effected at normal pressure or at an elevated pressure, preferably at normal pressure; any alkoxy group in the 8 or 9 position is generally not split off under these conditions; any nitro group is generally reduced to the amino group.

Process b) is the preferred process for the production of compounds having more than one hydroxy group.

The ether splitting of compounds of formula III wherein $R_2^{III}$ is —NHCOR$_5$, is conveniently effected under catalytic conditions; in this case $R_7$ preferably denotes benzyloxy.

It will be appreciated that insofar as similar reactions may be used for both precesses a) and b) for the splitting of ether groups, e.g. catalytic hydrogenation, then similar considerations apply to both processes.

The compounds of formula II are either known or may be produced in a manner analogous to known methods, e.g. for compounds of formula II wherein $R_1$ is other than hydrogen.

The production of compounds of formula II containing an amino group is preferably effected using the corresponding nitro compounds of formula II as starting materials, e.g. by selective reduction with nascent hydrogen, e.g. with iron shavings in an aqueous acid, optionally in an inert solvent, e.g. in a lower alkanol such as ethanol, preferably at an elevated temperature, e.g. at the boil.

The production of compounds of formula II containing an acylamino group is preferably effected by treating a compound of formula II containing an amino group with an acylating agent, e.g. a carboxylic acid chloride or anhydride, in the presence of an acid-binding agent, e.g. pyridine, optionally in an inert solvent and at an elevated temperature.

The production of compounds of formula II containing a dimethylamino group may, for example, be effected by reductive methylation of a compound of formula II containing an amino group with formaldehyde and formic acid as reducing agent (Leuckart-Wallach reaction).

The remaining compounds of formula II may, for example, be obtained by cyclization of the corresponding cis-4-benzoylamino-1-methyl-3-phenylpiperidine in accordance with Bischler-Napieralski.

The compounds of formula III may be produced in accordance with known methods, or using the methods described for the production of compounds of formulae I and II.

Insofar as the production of the required starting materials is not described, these are known or may be produced in accordance with known processes, or in a manner analogous to the processes described herein or to known processes.

Free base forms of compounds of formula I may be converted into acid addition salt forms in conventional manner and vice versa. Suitable acids for salt formation include maleic, hydrochloric and hydrobromic acids.

The compounds of formula I may be prepared in optically pure form using optically active starting materials in the above-mentioned process a) or b).

The optical isomers of formula I may be isolated in conventional manner, and may be purified to increase the optical purity in conventional manner.

The compounds of formula II and III in optically pure form may be obtained in conventional manner as described in our earlier invention from other starting materials which are optically active. It is preferred to obtain optically active starting materials by resolving a racemic compound of formula IV,

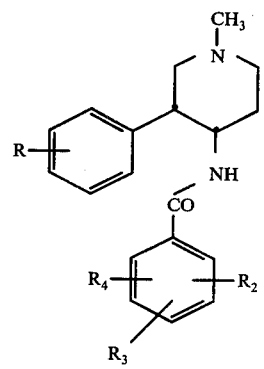

wherein
$R_2$, $R_3$ and $R_4$ are as defined above, and
R is $R_6$ or $R_7$ as defined above.

This resolution may be effected in analogous manner to that described in Example a) hereinafter, using if necessary a different optically active acid and different solvents. Any optically active isomer obtained may be purified in conventional manner, e.g. by fractional crystallization of a diastereoisomeric salt form or of the free base form.

An optically active compound of formula IV wherein R is $R_6$ as defined above may be cyclized to produce an optically active compound of formula II in conventional manner as described in Example b) hereinafter. An optically active compound of formula II wherein $R_6$ is alkoxy may be reduced in conventional manner to produce an optically active compound of formula III wherein $R_7$ is alkoxy, e.g. as described in Example c) hereinafter. Such a compound is also, it is appreciated, a compound of formula I.

One group of compounds comprises those having the same absolute configuration as (+)-cis-8-hydroxy-6-phenyl-2-methyl-1,2,3,4,4a,5,6,10b-octahydrobenzo[c][1,6]naphthyridine (hereinafter referred to as the A isomers). Another group (hereinafter referred to as the B isomers) comprises the optical antipodes of said one group.

In the following non-limitative Examples all temperatures are indicated in degrees Centigrade and are uncorrected.

EXAMPLE 1

Cis-8-hydroxy-2-methyl-6-phenyl-1,2,3,4,4a,5,6,10b-octahydrobenzo-[c][1,6]naphthyridine [process variant a)]

2 g of cis-8-hydroxy-2-methyl-6-phenyl-1,2,3,4,4a,10b-hexahydrobenzo[c][1,6]naphthyridine (M.P. of the dihydrobromide 268°–271°) are dissolved in 20 cc of methanol, and after the addition of 0.1 g of platinum oxide hydrogenation is effected at room temperature and normal pressure in an atmosphere of hydrogen. After the take up of hydrogen is complete the catalyst is filtered off and the filtrate es evaporated to dryness in a vacuum. The evaporation residue is dissolved in water, is made alkaline with potassium carbonate, is extracted thrice with methylene chloride, the organic phases are dried and evaporated to dryness, the residue is dissolved in alcohol, and a small excess of maleic acid is added, whereby the bishydrogen maleate of the title compound crystallizes (M.P. 196°–197°).

EXAMPLE 2

Cis-8-hydroxy-2-methyl-6-phenyl-1,2,3,4,4a5,6,10b-octahydrobenzo[c][1,6]naphthyridine [process variant a)]

1 g of cis-8-hydroxy-2-methyl-6-phenyl-1,2,3,4,4a10b-hexahydrobenzo[c][1,6]naphthyridine (M.P. of the dihydrobromide 268°–271°) is dissolved in 10 cc of ethanol, 0.1 g of sodium borohydride is added, and this reaction solution is boiled at reflux for 30 minutes. The excess sodium borohydride is decomposed by the addition of dilute hydrochloric acid, the solution is concentrated, is made strongly alkaline with dilute sodium hydroxide, and this alkaline aqueous solution is extracted with methylene chloride. After drying and evaporating the organic phase the residue is dissolved in ethanol and maleic acid is added, whereby the bishydrogen maleate of the title compound crystallizes (M.P. 196°–197°).

EXAMPLE 3

Cis-8-methoxy-2-methyl-6-phenyl-1,2,3,4,4a5,6,10b-octahydrobenzo-[c][1,6]naphthyridine The process is effected in a manner analogous to that described in Example 1 to 2, and the title compound is obtained by reduction of cis-8-methoxy-2-methyl-6-phenyl-1,2,3,4,4a, 10b-hexahydrobenzo[c][1,6]naphthyridine (M.P. of the bishydrogen maleate 146°–147° from ethanol). The title compound crystallizes from ethanol as bishydrogen maleate having an M.P. of 144°–145°.

Cis-8-methoxy-2-methyl-6-phenyl-1,2,3,4,4a, 10b-hexahydrobenzo[c][1,6]naphthyridine is obtained by addition of 3-amino-2-p-methoxyphenylpropionic acid ethyl ester to acrylic acid ethyl ester, reductive methylation of 2-p-methoxyphenyl-3,3'-iminodipropionic acid diethyl ester (M.P. of the hydrogen oxalate 152°) with formaldehyde to obtain 2-p-methoxymethyl-N-methyl-3,3'-iminodipropionic acid diethyl ester, reaction of the latter compound to obtain 3-carbethoxy-5-(p-methoxyphenyl)-1-methyl-4-piperidone (M.P. of the hydrochloride 180°–182°), which is converted by hydrolysis and subsequent decarboxylation into 3-p-methoxyphenyl-1-methyl-4-piperidone (M.P. of the hydrogen oxalate 137°–138°). The resulting piperidone is reacted with hydroxylamine to obtain 3-p-methoxyphenyl-1-methyl-4-piperidone oxime (M.P. 121°–122°), the oxime is hydrogenated with Raney nickel to obtain 4-amino-3-p-methoxyphenyl-1-methyl-piperidine (mixture of the two diastereoisomers), the amino compound is treated with benzoyl chloride, cis-4-benzoylamino-3-p-methoxyphenyl-1-methylpiperidine (M.P. 164°–165°) is isolated from the reaction mixture, and the latter amide is cyclized with phosphorus oxychloride to obtain the desired benzonaphthyridine.

EXAMPLE 4

Cis-6-(4-aminophenyl)-9-methoxy-2-methyl-1,2,3,4,4a,5,6,10b-octahydrobenzo[c][1,6]naphthyridine The process is effected in a manner analogous to that described in Example 1 or 2, and the title compound is obtained by reduction of cis-6-(4-aminophenyl)-9-methoxy-2-methyl-1,2,3,4,4a,10b-hexahydrobenzo[c][1,6]-naphthyridine (oil, crude). The title compound crystallizes from ethanol as trihydrochloride having an M.P. of 289°–291°.

The cis-6-(4-aminophenyl)-9-methoxy-2-methyl-1,2,3,4,4a, 10b-hexahydrobenzo[c][1,6]naphthyridine, required as starting material, is produced as follows:

2.7 g of iron shavings are added to a hot solution of 2 g of cis-9-methoxy-2-methyl-6-(4-nitrophenyl)-1,2,3,4,4a, 10b-hexahydrobenzo[c][1,6]naphthyridine (oil, crude, from ethyl acetate) in 40 cc of ethanol and 13 cc of water. A mixture of 13 cc of ethanol, 3 cc of water and 0.7 cc of 2 N hydrochloric acid is added dropwise thereto within 40 minutes while heating, and the reaction mixture is boiled at reflux for a further 3 hours. 1 cc of 2 N caustic soda solution is then added, filtration is effected, and the filtrate is concentrated by evaporation in a vacuum. The residue is dissolved in chloroform, the solution is dried over sodium sulphate, filtered and concentrated by evaporation in a vacuum, and the resulting viscous oil is used for the next reaction without purification.

EXAMPLE 5

Cis-6-(4-acetamidophenyl)-9-methoxy-2-methyl-1,2,3,4,4a,5,6,10b-octahydrobenzo[c][1,6]naphthyridine The process is effected in a manner analogous to that described in Example 1 or 2, and the title compound is obtained by reduction of cis-6-(4-acetamidophenyl)-9-methoxy-2-methyl-1,2,3,4,4a, 10b-hexahydrobenzo-[c][1,6]naphthyridine. The dihydrochloride of the title compound has an M.P. of 294°–296° from methanol.

The cis-6-(4-acetamidophenyl)-9-methoxy-2-methyl-1,2,3,4,4a, 10b-hexahydrobenzo[c][1,6]naphthyridine, required as starting material, is obtained from cis-6-(4-aminophenyl)-9-methoxy-2-methyl-1,2,3,4,4a, 10b-hexahydrobenzo[c][1,6]naphthyridine by allowing to stand over night at room temperature in the presence of acetic anhydride and pyridine. The resulting crude product (foam) is used as such for the next reaction.

EXAMPLE 6

Cis-6-(4-dimethylaminophenyl)-9-methoxy-2-methyl-1,2,3,4,4a,5,6,10b-octahydrobenzo[c][1,6]naphthyridine The process is effected in a manner analogous to that described in Example 1 or 2, and the title compound is obtained by reduction of cis-6-(4-dimethylaminophenyl)-9-methoxy-2-methyl-1,2,3,4,4a,10b-hexahydrobenzo-[c][1,6]naphthyridine. The dihydrochloride of the title compound has an M.P. of 275°–277°.

The cis-6-(4-dimethylaminophenyl)-9-methoxy-2-methyl-1,2,3,4,4a,10b-hexahydrobenzo[c][1,6]naphthyridine, required as starting material, is obtained in accordance with Leuckart-Wallach from cis-6-(4-aminophenyl)-9-methoxy-2-methyl-1,2,3,4,4a, 10b-hexahydrobenzo[c][1,6]-naphthyridine by reductive dimethylation with formaldehyde and formic acid. The resulting crude product is used as such for the next reaction.

| Ex. Nr. | Analogous to Ex. | $R_2$ | $R_3$ | $R_4$ | $R_1$ | Salt form | M.P. |
|---|---|---|---|---|---|---|---|
| 7 | 1,2 | 4-F | H | H | 9-MeO | Dihydrochloride | 312–315° |
| 8 | 1,2 | 4-Me | H | H | 9-MeO | " | 332–335° |
| 9 | 1,2 | 4-Cl | H | H | 9-MeO | " | 290–292° |
| 10 | 1,2 | 4-Cl | H | H | H | " | 265–269° |

-continued

| Ex. Nr. | Analogous to Ex. | $R_2$ | $R_3$ | $R_4$ | $R_1$ | Salt form | M.P. |
|---|---|---|---|---|---|---|---|
| 11 | 1,2 | 4-Me | H | H | H | Bishydrogen maleate | 196–197° |
| 12 | 1,2 | 3-MeO | 4-MeO | H | H | " | 168–169° |
| 13 | 1,2 | 3-MeO | 4-MeO | 5-MeO | H | Dihydrochloride | 302–304° |
| 14 | 1,2 | 3-Cl | 4-Cl | H | H | " | 279–281° |
| 15 | 1,2 | H | H | H | 9-MeO | " | 316–319° |
| 16 | 1,2 | 3-MeO | 4-MeO | 5-MeO | 8-MeO | Bishydrogen maleate | 168–170° |
| 17 | 1,2 | 4-F | H | H | 8-MeO | Dihydrochloride | 270–273° |
| 18 | 1,2 | 4-MeO | H | H | 8-MeO | Bishydrogen maleate | 155–156° |
| 19 | 1,2 | 3-MeO | 4-MeO | H | 9-MeO | Dihydrochloride | 272–275° |
| 20 | 1,2 | 3-Cl | 4-Cl | H | 9-MeO | " | 301–304° |
| 21 | 1,2 | 3-MeO | 4-MeO | 5-MeO | 9-MeO | " | 288–290° |
| 22 | 1 | 3-OH | 4-OH | H | H | Dihydrobromide | 277–279° |
| 23 | 1 | 4-OH | H | H | 8-OH | " | 315–316° |
| 24 | 1 | 3-OH | 4-OH | 5-OH | H | " | 283–285° |
| 25 | 1* | 3-OH | 4-OH | H | 9-MeO | Dihydrochloride | 295–298° |
| 26 | 1* | 4-OH | H | H | 9-MeO | " | 312–315° |
| 27 | 1* | 2-OH | H | H | 9-MeO | " | 275–280° |
| 28 | 1,2 | H | H | H | 9-OH | Dihydrobromide | 292–294° |
| 29 | 1 | 3-OH | 4-OH | H | 8-OH | " | 310–313° |
| 30 | 1,2 | 3-Cl | 4-Cl | H | 8-OH | Bishydrogen maleate | 167–170° |
| 31 | 1,2 | 3-Me | 4-Me | H | 8-OH | Dihydrobromide | 340–342° |
| 32 | 1,2 | 4-Cl | H | H | 8-OH | — | 278–280° |
| 33 | 1,2 | 4-F | H | H | 8-OH | Dihydrobromide | 322–325° |
| 34 | 1 | 3-OH | 4-OH | 5-OH | 8-OH | " | 298–300° |
| 35 | 1,2 | 4-$NH_2$ | H | H | 8-OH | Trihydrochloride | 266–269° |
| 36 | 1,2 | H | H | H | H | Bishydrogen maleate | 175–176° |
| 37 | 2 | 4-$NO_2$ | H | H | 9-MeO | Dihydrochloride | 248–251° |
| 38 | 1,2 | 4-$NH_2$ | H | H | 8-MeO | Trihydrochloride | 254–255° |
| 39 | 1,2 | 4-NHCOCH$_3$ | H | H | 8-OH | — | 275–277° |
| 39a | 2 | 4-O.CH$_2$.C$_6$H$_5$ | H | H | H | — | |

*Using as starting material the corresponding compounds of formula II with each hydroxy group replaced by a benzyloxy group, and as catalyst palladium in place of platinum.

EXAMPLE 40

Cis-8-hydroxy-6-phenyl-2-methyl-1,2,3,4,4a,5,6,10b-octahydrobenzo[c][1,6]naphthyridine [process variant b)]

2 g of cis-8-methoxy-6-phenyl-2-methyl-1,2,3,4,4a,5,6,10b-octahydrobenzo[c][1,6]naphthyridine bishydrogen maleate (M.P. 144°–145° from ethanol) are converted into the free base in the usual manner. This is then boiled at reflux with 20 cc of 60% hydrobromic acid for 2 hours. The residue obtained after evaporating to dryness in a vacuum is recrystallized from alcohol. The bishydrogen maleate of the title compound has a M.P. of 196°–197°.

EXAMPLE 41

Cis-6-(4-hydroxyphenyl)-9-methoxy-2-methyl-1,2,3,4,4a,5,6,10b-octahydrobenzo[c][1,6]naphthyridine [process variant b)]

5 g of cis-6-(4-benzyloxyphenyl)-9-methoxy-2-methyl-1,2,3,4,4a,5,6,10b-octahydrobenzo[c][1,6]-naphthyridine are dissolved in 50 cc of ethanol, and after the addition of 5 g of palladium (10% on aluminium oxide) hydrogenation is effected at room temperature and normal pressure in an atmosphere of hydrogen until the take up of hydrogen is complete. The dihydrochloride of the resulting title compound has an M.P. of 312°–315° from ethanol.

| Ex. Nr. | Analogous to Ex. | $R_2^{II}$ | $R_3^{II}$ | $R_4^{II}$ | Position of the OH group | Salt form | M.P. |
|---|---|---|---|---|---|---|---|
| 42 | 40,41 | H | H | H | 9- | Dihydrobromide | 292–294° |
| 43 | 40,41 | 3-OH | 4-OH | H | 8- | " | 310–313° |
| 44 | 40,41 | 3-Cl | 4-Cl | H | 8- | Bishydrogen maleate | 167–170° |
| 45 | 40,41 | 3-Me | 4-Me | H | 8- | Dihydrobromide | 340–342° |
| 46 | 40,41 | 4-Cl | H | H | 8- | — | 278–280° |
| 47 | 40,41 | 4-F | H | H | 8- | Dihydrobromide | 322–325° |
| 48 | 40,41 | 3-OH | 4-OH | 5-OH | 8- | " | 298–300° |
| 49 | 40,41 | 4-$NH_2$ | H | H | 8- | Trihydrochloride | 266–269° |
| 50 | 40,41 | 4-OH | H | H | 8- | Dihydrobromide | 315–316° |
| 51 | 41 | 4-NHCOCH$_3$ | H | H | 8- | — | 275–277° |
| 52 | 41 | H | H | H | 8- | Bishydrogen maleate | 196–197° |

Preparation of (+)-cis-8-hydroxy-6-phenyl-2-methyl-1,2,3,4,4a,5,6,10b-octahydrobenzo[c][1,6]naphthyridine (a) 5.0 g (15.4 m Mol) of racemic cis-4-benzoylamino-3-p-methoxyphenyl-1-methylpiperidine and 2.31 g (15.4 m Mol) of D-tartaric acid were dissolved together in 90 ml of water using a slight amount of warming. The solution was evaporated to about half its original volume under a vacuum. The concentrated solution was allowed to stand overnight. The D-tartrate salt which crystallized out was converted into the corresponding crystalline free base by treatment with 2N sodium hydroxide solution and methylene chloride. The base, (−)-cis-4-benzoylamino-3-p-methoxyphenyl-1-methylpiperidine, exhibited the following specific rotation :-[$\alpha$]$_{578}$ = − 67.2°; [c = 1 in CHCl$_3$]. A sample of this base was converted as indicated above into the D-tartrate salt and this salt was again converted into the free base, which had substantially the same specific rotation as the previously obtained sample. (b) 5.0 g of (−)-cis-4-benzoylamino-3-p-methoxyphenyl-1-methylpiperidine and 100 ml POCl$_3$ (previously activated by 3% v/v of water) were boiled under reflux for three hours. The reaction mixture was worked up in conventional manner to yield the dihydrochloride of (+)-cis-8-methoxy-2-methyl-6-phenyl-1,2,3,4,4a,10b-hexahydrobenzo[c][1,6]naphthyridine m.p. 245°-8°. The corresponding free base was a bright yellow oil having a specific rotation $[\alpha]_{578} = +276°$ (c = 1.0 in CHCl$_3$). (c) 2.3 g of (+)-cis 8-methoxy-2-methyl-6-phenyl-1,2,3,4,4a,10b-hexahydrobenzo[c][1,6]naphthyridine was reduced with 0.5 g NaBH$_4$ in 100 ml ethanol at room temperature over one hour. After working up in conventional manner (−)-cis-8-methoxy-2-methyl-6-phenyl-1,2,3,4,4a,5,6,10b-octahydrobenzo[c][1,6]naphthyridine in free base form as a yellow oil was obtained $[\alpha]_{578} = -9.5°$ (c = 1.0 in CHCl$_3$). (d) 2.17 g of (−)-cis-8-methoxy-2-methyl-6-phenyl-1,2,3,4,4a,5,6,10b-octahydrobenzo[c][1,6]naphthyridine in free base form, and 50 ml of conc. HCl were heated in a sealed tube in an oil bath at 125°. The reaction solution was evaporated to dryness and the yellow residue was boiled with ethanol. (+)-cis-8-hydroxy-2-methyl-6-phenyl-1,2,3,4,4a,5,6,10b-octahydrobenzo[c][1,6]naphthyridine in dihydrochloride form crystallized out as white crystals $[\alpha]_{578} +100°$; $[\alpha]_{546} +115°$; $[\alpha]_{436} +212°$ (c = 1.0 in CHCl$_3$) m.p. 324°-6°.

(−)-cis-8-hydroxy-6-phenyl-2-methyl-1,2,3,4,4a,5,6,10b-octahydrobenzo[c][1,6]naphthyridine is prepared in analogous manner using L-tartaric acid in step a) instead of D-tertaric acid. In the final step d) the (+)-8-methoxy derivative ($[\alpha]_{578} +7.2°$ (c = 1.0 in CHCl$_3$) ) is demethylated to yield the (−)-cis compound having, in dihydrochloride form, $[\alpha]_{578} -98°$ (c = 1.0 in CHCl$_3$) M.Pt. 325° - 327°.

The compounds of formula I are useful as agents for the treatment of allergies, e.g. dermatosis and rhinitis and as bronchospasmolitics, as indicated in standard tests, e.g. by an inhibition of the bronchospasms induced by histamine in guinea pigs or cats following the method of H. Konzett and R. Rossler [Arch. Exper. Path. Pharmacol. 195 71 (1940)]. In this test the compounds are administered i.v. at a dose of from about 0.5 to about 30 mg/kg animal body weight.

The compounds of formula I, especially the B isomers, are particularly useful additionally as agents for the treatment of asthma, e.g. allergic asthma, and bronchitis e.g. against reflex-bronchoconstrictions, as indicated by an inhibition of the bronchospasms induced by acetylcholine in guinea pigs following the method of H. Konzett and R. Rossler mentioned above. In this test the compounds are administered i.v. at a dose of from about 0.1 to 1 mg/kg animal body weight.

For these uses the dosage will, of course, vary depending on the compound employed, mode of administration and treatment desired. However, in general, satisfactory results are obtained when administered at a daily dosage of from about 0.05 mg to about 50 mg per kg animal body weight, conveniently given in divided doses 2 to 4 times a day or in sustained release form. For the larger mammals, the total daily dosage especially for the B isomers is in the range from about 2 to about 700 mg, and dosage forms suitable for oral administration comprise from about 0.5 mg to about 350 mg of the compounds admixed with a solid or liquid pharmaceutical carrier or diluent.

For the B isomer obtained in example d) a satisfactory daily dose is from 2 to 20 mg.

For the racemic compounds, for the larger mammal, the total daily dosage is in the range from about 35 to about 700 mg, and dosage forms suitable for oral administration comprise from about 6 mg to about 350 mg of the compounds admixed with a solid or liquid pharmaceutical carrier or diluent.

For the A isomers, for the larger mammals, the total daily dosage is in the range from about 10 to about 100 mg, and dosage forms suitable for oral administration comprise from about 2.5 mg to about 50 mg of the compounds admixed with a solid or liquid pharmaceutical carrier or diluent.

For the A isomer obtained in Example d) a satisfactory daily dose is from 10 to 100 mg.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastro-intestinal tract and thereby provide sustained action over a long period.

The preferred compositions from the standpoint of ease of administration are solid compositions, particularly solid-filled gelatin capsules and tablets.

Compositions for inhalation therapy may be prepared in conventional manner, e.g. in the form of nebulizers, vaporizers and aerosols. Unit doses may be provided by a metered value system. Such compositions are especially useful for the bronchospasmolytic use of the compounds. Propellants that may be used in such compositions include fluorinated hydrocarbons.

We claim:

1. A compound of formula I,

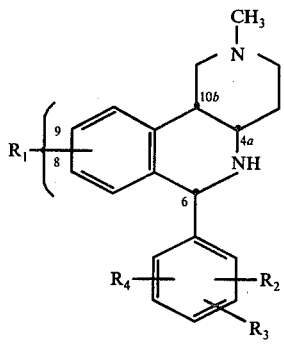

wherein the indicated radical in the 8 or 9 position of the benzonaphthyridine structure ($R_1$) is hydrogen, alkoxy of 1 to 4 carbon atoms or hydroxy, and (i)
$R_2$ hydrogen, alkyl of 1 to 4 carbon atoms, alkoxy of 1 to 4 carbon atoms, benzyloxy, hydroxy, halogen, nitro, amino, dimethylamino, or —NHCOR$_5$ wherein $R_5$ is hydrogen or alkyl of 1 to 4 carbon atoms, and $R_3$ and $R_4$ are hydrogen, or (ii)
$R_2$ is alkyl of 1 to 4 carbon atoms, alkoxy of 1 to 4 carbon atoms, benzyloxy, hydroxy, halogen or nitro, $R_3$ is alkyl of 1 to 4 carbon atoms, alkoxy of 1 to 4 carbon atoms, benzyloxy, hydroxy or chlorine, and $R_4$ is hydrogen, (iii)
$R_2$, $R_3$ and $R_4$ are, independently, alkoxy of 1 to 4 carbon atoms or benzyloxy, or (iv)
$R_2$, $R_3$ and $R_4$ are, independently, alkyl of 1 to 4 carbon atoms, or (v)
$R_2$, $R_3$ and $R_4$ are hydroxy, with the proviso that (i) when one of the radicals $R_2$, $R_3$ and $R_4$ is benzyloxy, the indicated radical in the 8 or 9 position of the benzonaphthyridine structure ($R_1$) is hydrogen or alkoxy of 1 to 4 carbon atoms, (ii) when the indicated radical in the 8 or 9 position of the benzonaphthyridine structure ($R_1$) is other than hydrogen or alkoxy and is in the 9 position, each of the radicals $R_2$, $R_3$ and $R_4$ is other than alkoxy of 1 to 4 carbon atoms, and (iii) when one of the radicals $R_2$ and $R_3$ is benzyloxy or alkoxy of 1 to 4 carbon atoms, the remaining radical $R_2$ or $R_3$ is other than hydroxy, in free base form or in pharmaceutically acceptable acid addition salt form, in racemic form or in optically active form.

2. A pharmaceutical composition useful as a bronchospasmolytic comprising a therapeutically effective amount of a compound of claim 1 in association with a pharmaceutical carrier or diluent.

3. A method of treating bronchospasms in animals, which comprises administering a therapeutically effective amount of a compound of claim 1 to an animal in need of such treatment.

4. A compound of claim 1 wherein
$R_2$ is hydrogen, alkyl of 1 to 4 carbon atoms, alkoxy of 1 to 4 carbon atoms, benzyloxy, hydroxy, halogen, nitro, amino, dimethylamino, or —NHCOR$_5$ wherein $R_5$ is hydrogen or alkyl of 1 to 4 carbon atoms, and
$R_3$ and $R_4$ are hydrogen.

5. A compound of claim 1 wherein
$R_2$ is alkyl of 1 to 4 carbon atoms, alkoxy of 1 to 4 carbon atoms, benzyloxy, hydroxy, halogen or nitro,
$R_3$ is alkyl of 1 to 4 carbon atoms, alkoxy of 1 to 4 carbon atoms, benzyloxy, hydroxy or chlorine, and
$R_4$ is hydrogen.

6. A compound of claim 1 wherein $R_2$, $R_3$ and $R_4$ are, independently, alkoxy of 1 to 4 carbon atoms or benzyloxy.

7. A compound of claim 1 wherein $R_2$, $R_3$ and $R_4$ are, independently, alkyl of 1 to 4 carbon atoms.

8. A compound of claim 1 wherein $R_2$, $R_3$ and $R_4$ are hydroxy.

9. The compound of claim 1 which is cis-8-hydroxy-2-methyl-6-phenyl-1,2,3,4,4a,5,6,10b-octahydrobenzo-[c][1,6]naphthyridine.

10. The compound of claim 1 which is cis-8-methoxy-2-methyl-6-phenyl-1,2,3,4,4a,5,6,10b-octahydrobenzo-[c][1,6]naphthyridine.

11. The compound of claim 1 which is cis-6-(4-aminophenyl)-9-methoxy-2-methyl-1,2,3,4,4a,5,6,10b-octahydrobenzo-[c][1,6]-naphthyridine.

12. The compound of claim 1 which is cis-6-(4-acetamidophenyl)-9-methoxy-2-methyl-1,2,3,4,4a,5,6,10b-octahydrobenzo-[c][1,6]naphthyridine.

13. The compound of claim 1 which is cis-6-(4-dimethylaminophenyl)-9-methoxy-2-methyl-1,2,3,4,4a,5,6,10b-octahydrobenzo-[c][1,6]naphthyridine.

14. The compound of claim 1 wherein $R_2$, $R_3$, $R_4$ and $R_1$ are respectively 4-F, H, H, 9-MeO.

15. The compound of claim 1 wherein $R_2$, $R_3$, $R_4$ and $R_1$ are respectively 4-Me, H, H, 9-MeO.

16. The compound of claim 1 wherein $R_2$, $R_3$, $R_4$ and $R_1$ are respectively 4-Cl, H, H, 9-MeO.

17. The compound of claim 1 wherein $R_2$, $R_3$, $R_4$ and $R_1$ are respectively 4-Cl, H, H, H.

18. The compound of claim 1 wherein $R_2$, $R_3$, $R_4$ and $R_1$ are respectively 4-Me, H, H, H.

19. The compound of claim 1 wherein $R_2$, $R_3$, $R_4$ and $R_1$ are respectively 3-MeO, 4-MeO, H, H.

20. The compound of claim 1 wherein $R_2$, $R_3$, $R_4$ and $R_1$ are respectively 3-MeO, 4-MeO, 5-MeO, H.

21. The compound of claim 1 wherein $R_2$, $R_3$, $R_4$ and $R_1$ are respectively 3-Cl, 4-Cl, H, H.

22. The compound of claim 1 wherein $R_2$, $R_3$, $R_4$ and $R_1$ are respectively H, H, H, 9-MeO.

23. The compound of claim 1 wherein $R_2$, $R_3$, $R_4$ and $R_1$ are respectively 3-MeO, 4-MeO, 5-MeO, 8-MeO.

24. The compound of claim 1 wherein $R_2$, $R_3$, $R_4$ and $R_1$ are respectively 4-F, H, H, 8-MeO.

25. The compound of claim 1 wherein $R_2$, $R_3$, $R_4$ and $R_1$ are respectively 4-MeO, H, H, 8-MeO.

26. The compound of claim 1 wherein $R_2$, $R_3$, $R_4$ and $R_1$ are respectively 3-MeO, 4-MeO, H, 9-MeO.

27. The compound of claim 1 wherein $R_2$, $R_3$, $R_4$ and $R_1$ are respectively 3-Cl, 4-Cl, H, 9-MeO.

28. The compound of claim 1 wherein $R_2$, $R_3$, $R_4$ and $R_1$ are respectively 3-MeO, 4-MeO, 5-MeO, 9-MeO.

29. The compound of claim 1 wherein $R_2$, $R_3$, $R_4$ and $R_1$ are respectively 3-OH, 4-OH, H, H.

30. The compound of claim 1 wherein $R_2$, $R_3$, $R_4$ and $R_1$ are respectively 4-OH, H, H, 8-OH.

31. The compound of claim 1 wherein $R_2$, $R_3$, $R_4$ and $R_1$ are respectively 3-OH, 4-OH, 5-OH, H.

32. The compound of claim 1 wherein $R_2$, $R_3$, $R_4$ and $R_1$ are respectively 3-OH, 4-OH, H, 9-MeO.

33. The compound of claim 1 wherein $R_2$, $R_3$, $R_4$ and $R_1$ are respectively 4-OH, H, H, 9-MeO.

34. The compound of claim 1 wherein $R_2$, $R_3$, $R_4$ and $R_1$ are respectively 2-OH, H, H, 9-MeO.

35. The compound of claim 1 wherein $R_2$, $R_3$, $R_4$ and $R_1$ are respectively H, H, H, 9-OH.

36. The compound of claim 1 wherein $R_2$, $R_3$, $R_4$ and $R_1$ are respectively 3-OH, 4-OH, H, 8-OH.

37. The compound of claim 1 wherein $R_2$, $R_3$, $R_4$ and $R_1$ are respectively 3-Cl, 4-Cl, H, 8-OH.

38. The compound of claim 1 wherein $R_2$, $R_3$, $R_4$ and $R_1$ are respectively 3-Me, 4-Me, H, 8-OH.

39. The compound of claim 1 wherein $R_2$, $R_3$, $R_4$ and $R_1$ are respectively 4-Cl, H, H, 8-OH.

40. The compound of claim 1 wherein $R_2$, $R_3$, $R_4$ and $R_1$ are respectively 4-F, H, H, 8-OH.

41. The compound of claim 1 wherein $R_2$, $R_3$, $R_4$ and $R_1$ are respectively 3-OH, 4-OH, 5-OH, 8-OH.

42. The compound of claim 1 wherein $R_2$, $R_3$, $R_4$ and $R_1$ are respectively 4-$NH_2$, H, H, 8-OH.

43. The compound of claim 1 wherein $R_2$, $R_3$, $R_4$ and $R_1$ are respectively H, H, H, H.

44. The compound of claim 1 wherein $R_2$, $R_3$, $R_4$ and $R_1$ are respectively 4-$NO_2$, H, H, 9-MeO.

45. The compound of claim 1 wherein $R_2$, $R_3$, $R_4$ and $R_1$ are respectively 4-$NH_2$, H, H, 8-MeO.

46. The compound of claim 1 wherein $R_2$, $R_3$, $R_4$ and $R_1$ are respectively 4-$NHCOCH_3$, H, H, 8-OH.

47. The compound of claim 1 wherein $R_2$, $R_3$, $R_4$ and $R_1$ are respectively 4-$O.CH_2.C_6H_5$, H, H, H.

48. A compound of claim 1 wherein $R_1$ is hydroxy.

49. A compound of claim 48 wherein $R_1$ is in the 8-position.

50. A compound of claim 1 wherein $R_1$ is alkoxy.

51. A compound of claim 50 wherein $R_1$ is in the 8-position.

52. A compound of claim 1 in racemic form.

53. A compound of claim 1 in optically pure form.

54. A compound of claim 53 having the same absolute configuration at the 4a, 6 and 10 positions as (+)-cis-8-hydroxy-6-phenyl-2-methyl-1,2,3,4,4a,5,6,10b-octahydrobenzo[c][1,6]naphthyridine.

55. A compound of claim 54 which is (+)-cis-8-hydroxy-6-phenyl-2-methyl-1,2,3,4,4a,5,6,10b-octahydrobenzo[c][1,6]naphthyridine.

56. A compound of claim 54 which is (−)-cis-8-methoxy-6-phenyl-2-methyl-1,2,3,4,4a,5,6,10b-octahydrobenzo[c][1,6]naphthyridine.

57. A compound of claim 53 having the same absolute configuration at the 4a, 6 and 10 positions as (−)-cis-8-hydroxy-6-phenyl-2-methyl-1,2,3,4,4a,5,6,10b-octahydrobenzo[c][1,6]naphthyridine.

58. A compound of claim 57 which is (−)-cis-8-hydroxy-6-phenyl-2-methyl-1,2,3,4,4a,5,6,10b-octahydrobenzo[c][1,6]naphthyridine.

59. A compound of claim 57 which is (+)-cis-8-methoxy-6-phenyl-2-methyl-1,2,3,4,4a,5,6,10b-octahydrobenzo[c][1,6]naphthyridine.

60. A method of treating allerges in animals which comprises administering a therapeutically effective amount of a compound of claim 1 to an animal in need of such treatment.

61. The method of claim 60, wherein the allergy is a dermatosis.

62. The method of claim 60, wherein the allergy is a rhinitis.

63. A method of treating asthma in animals which comprises administering a therapeutically effective amount of a compound of claim 1 to an animal in need of such treatment.

64. The method of claim 63, wherein the asthma is allergic asthma.

65. A method of treating bronchitis in animals which comprises administering a therapeutically effective amount of a compound of claim 1 to an animal in need of such treatment.

66. The method of claim 65, wherein the bronchitis is associated with reflex-bronchoconstrictions.

67. A compound of claim 1 having the formula,

Ia wherein $R_2$, $R_3$ and $R_4$ are as defined above with the proviso thereto and the further proviso that (iv) each of $R_2$, $R_3$ and $R_4$ is other than benzyloxy.

68. A pharmaceutical composition according to claim 2, comprising 0.5 to 350 milligrams of the compound per unit dosage.

69. A pharmaceutical composition according to claim 2 in which the compound is cis-8-hydroxy-2-methyl-6-phenyl-1,2,3,4,4a,5,6,10b-octahydrobenzo[c][1,6]naphthyridine.

70. A method according to claim 3 in which 2 to 700 milligrams of the compound are administered daily.

71. A method according to claim 3 in which 0.5 to 350 milligrams of the compound are administered per unit dosage.

72. A method according to claim 3 in which the compound is cis-8-hydroxy-2-methyl-6-phenyl-1,2,3,4,4a,5,6,10b-octahydrobenzo-[c][1,2]naphthyridine.

* * * * *